(12) United States Patent
Cheng et al.

(10) Patent No.: US 11,117,157 B2
(45) Date of Patent: Sep. 14, 2021

(54) NEBULIZER

(71) Applicant: HEALTH & LIFE CO., LTD., New Taipei (TW)

(72) Inventors: Yi-Ping Cheng, New Taipei (TW); Shao-Ming Tien, New Taipei (TW)

(73) Assignee: HEALTH & LIFE CO., LTD., New Taipei (TW)

( * ) Notice: Subject to any disclaimer, the term of this patent is extended or adjusted under 35 U.S.C. 154(b) by 20 days.

(21) Appl. No.: 15/931,308

(22) Filed: May 13, 2020

(65) Prior Publication Data

US 2020/0360959 A1 Nov. 19, 2020

(30) Foreign Application Priority Data

May 16, 2019 (TW) .................................. 108206127

(51) Int. Cl.
*B05B 17/06* (2006.01)
*B05B 5/00* (2006.01)
*B05B 17/00* (2006.01)

(52) U.S. Cl.
CPC .......... *B05B 17/0653* (2013.01); *B05B 5/006* (2013.01); *B05B 17/0646* (2013.01)

(58) Field of Classification Search
CPC . B05B 5/006; B05B 17/0646; B05B 17/0653; B05B 17/0669
See application file for complete search history.

(56) References Cited

U.S. PATENT DOCUMENTS

| 5,910,698 | A  | * | 6/1999 | Yagi ....................... G05D 19/02 310/316.03 |
| 10,653,178 | B1 | * | 5/2020 | Kerr ..................... B05B 17/0607 |
| 2002/0129813 | A1 | * | 9/2002 | Litherland .......... B05B 17/0646 128/200.16 |
| 2009/0242662 | A1 | * | 10/2009 | Lu ....................... B05B 17/0646 239/102.2 |
| 2011/0030678 | A1 | * | 2/2011 | Power ................. A61M 13/003 128/200.14 |
| 2013/0277446 | A1 | * | 10/2013 | Selby .................... B06B 1/0688 239/4 |
| 2013/0291859 | A1 | * | 11/2013 | Casey .................... B05B 12/00 128/200.14 |

* cited by examiner

*Primary Examiner* — Ryan A Reis
(74) *Attorney, Agent, or Firm* — Hamre, Schumann, Mueller & Larson, P.C.

(57) ABSTRACT

A nebulizer includes an aerosolizer, a controller, a power converter, a power source and a voltage detector. When the aerosolizer is requested to eject aerosolized liquid at a standard spraying speed, the controller sets a parameter value of a conversion parameter based on a stored standard value, transmits the parameter value to the power converter, and controls the power source to supply electric power. The power converter converts the electric power based on the parameter value to power the aerosolizer. Based on a stored expected value and a detected value generated by the voltage detector in response to operation of the aerosolizer, the controller controls the power source to adjust the voltage of the electric power supplied thereby.

12 Claims, 6 Drawing Sheets

| Input device | Controller | Power source | Power converter | Aerosolizer |
|---|---|---|---|---|
| Generating and outputting input signal to controller — 50 | — 51 | Supplying electric power to power converter — 53 | Converting electric power for powering aerosolizer — 54 | Vibrating to aerosolize liquid, and ejecting aerosolized liquid — 55 → To step 56 |
| | Setting parameter value of conversion parameter to be equal to standard resonant-frequency value, and transmitting parameter value to power converter | | | |
| | Controlling power source to supply electric power — 52 | | | |

| Input device | Controller | Power source | Power converter | Aerosolizer |
|---|---|---|---|---|
| 70 — Generating and outputting input signal to controller | 71 — Executing calibration procedure, and obtaining target voltage value<br><br>72 — Generating and transmitting power adjusting signal to power source | 73 — Adjusting electric power being supplied to power converter | 74 — Converting electric power for powering aerosolizer | 75 — Vibrating to aerosolize liquid, and ejecting aerosolized liquid |

FIG. 6

NEBULIZER

CROSS-REFERENCE TO RELATED APPLICATION

This application claims priority of Taiwanese Invention Patent Application No. 108206127, filed on May 16, 2019.

FIELD

The disclosure relates to a nebulizer, and more particularly to a nebulizer capable of calibrating spraying speed.

BACKGROUND

Conventionally, inconsistency in spraying speed is often found between nebulizers of the same model even if the nebulizers are produced through the same manufacturing process. The inconsistency in the spraying speed may be attributed to inconsistent vibration frequencies among piezoelectric vibrators in the nebulizers, where the vibration of the piezoelectric vibrator is utilized to achieve liquid aerosolization for the nebulizer. The inconsistent vibration frequencies may stem from the lowest resonant frequency of the piezoelectric vibrator of one nebulizer being different from that of another nebulizer, or may be due to inconsistency in the voltage and/or frequency of electric power supplied to the nebulizers.

SUMMARY

Therefore, an object of the disclosure is to provide a nebulizer capable of calibrating spraying speed and a method for calibrating spraying speed of the nebulizer that can alleviate at least one of the drawbacks of the prior art.

According to one aspect of the disclosure, the nebulizer capable of calibrating spraying speed includes a container and a host device separably coupled to the container.

The container includes a containing body that is configured to accommodate liquid, an aerosolizer that is disposed on the containing body, and a container data storage that is disposed on the containing body.

The aerosolizer is configured to aerosolize the liquid accommodated in the containing body by vibration to result in aerosolized liquid, and to eject the aerosolized liquid.

The container data storage is configured to store a standard resonant-frequency value which corresponds to a standard spraying speed of the aerosolizer, and an expected feedback-voltage value which is related to the standard resonant-frequency value.

The host device includes a power source that is configured to supply electric power, a power converter that is electrically connected to the power source and the aerosolizer, a voltage detector that is electrically connected to the aerosolizer, and a controller that is electrically connected to the aerosolizer, the container data storage, the power source, the voltage detector and the power converter.

The voltage detector is configured to continuously detect a feedback voltage coming from the aerosolizer, and to generate a detected feedback-voltage value which indicates a current measurement result of the feedback voltage.

The controller is configured to, in response to receipt of an input signal that requests operation of the aerosolizer at the standard spraying speed, read the standard resonant-frequency value stored in the container data storage, make a parameter value of a conversion parameter equal the standard resonant-frequency value, transmit the parameter value to the power converter, and control the power source to supply electric power.

The power converter is configured to, based on the parameter value, convert the electric power supplied by the power source into converted electric power by changing at least one of voltage or frequency of the electric power, and to provide the converted electric power to the aerosolizer so as to enable the aerosolizer to vibrate based on the converted electric power and to generate the feedback-voltage.

The controller is further configured to, based on the detected feedback-voltage value generated by the voltage detector and the expected feedback-voltage value stored in the container data storage, repeatedly control the power source to adjust the voltage of the electric power supplied thereby until it is determined that the detected feedback-voltage value matches the expected feedback-voltage value.

According to another aspect of the disclosure, the method is to be implemented by the nebulizer that is previously described, the method includes steps of:

a) by the controller in response to receipt of the input signal that requests operation of the aerosolizer at the standard spraying speed, reading the standard resonant-frequency value stored in the container data storage, making the parameter value of the conversion parameter equal the standard resonant-frequency value, transmitting the parameter value to the power converter, and controlling the power source to supply electric power;

b) by the power converter, converting the electric power supplied by the power source into converted electric power based on the parameter value, and providing the converted electric power to the aerosolizer so as to enable the aerosolizer to vibrate based on the converted electric power; and c) by the controller based on the detected feedback-voltage value generated by the voltage detector and the expected feedback-voltage value stored in the container data storage, repeatedly controlling the power source to adjust the voltage of the electric power supplied thereby until it is determined that the detected feedback-voltage value matches the expected feedback-voltage value.

BRIEF DESCRIPTION OF THE DRAWINGS

Other features and advantages of the disclosure will become apparent in the following detailed description of the embodiment with reference to the accompanying drawings, of which.

DETAILED DESCRIPTION

Before the disclosure is described in greater detail, it should be noted that where considered appropriate, reference numerals or terminal portions of reference numerals have been repeated among the figures to indicate corresponding or analogous elements, which may optionally have similar characteristics.

Figure 1:
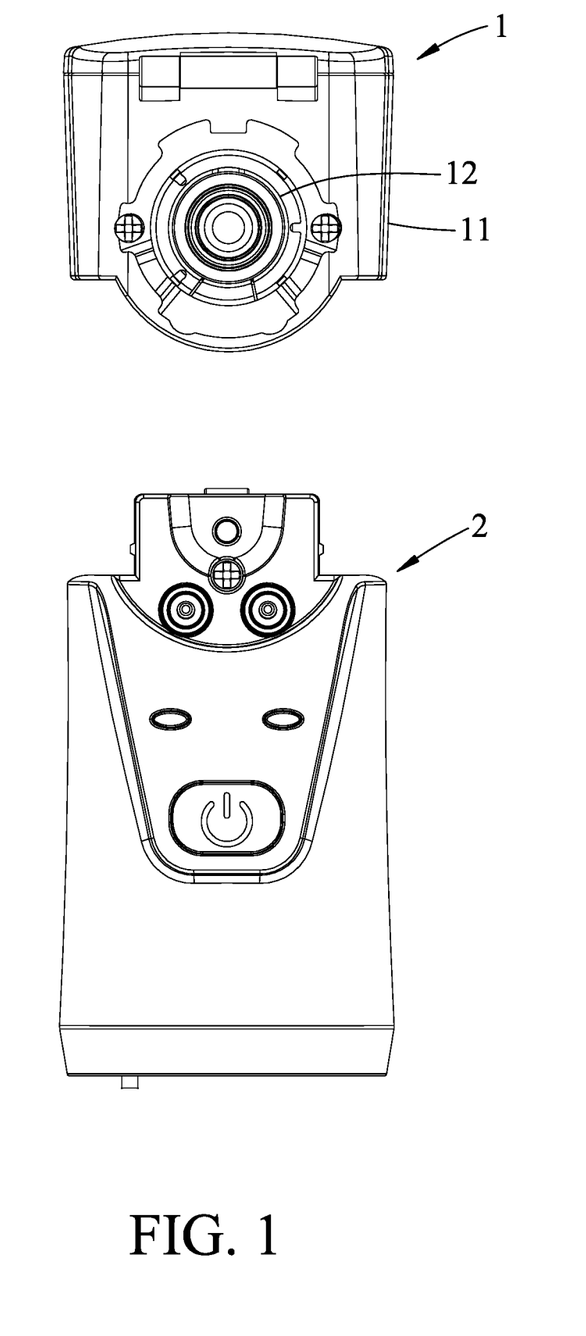
FIG. 1 is schematic front view illustrating an embodiment of a nebulizer capable of calibrating spraying speed according to the disclosure.
Figure 2:
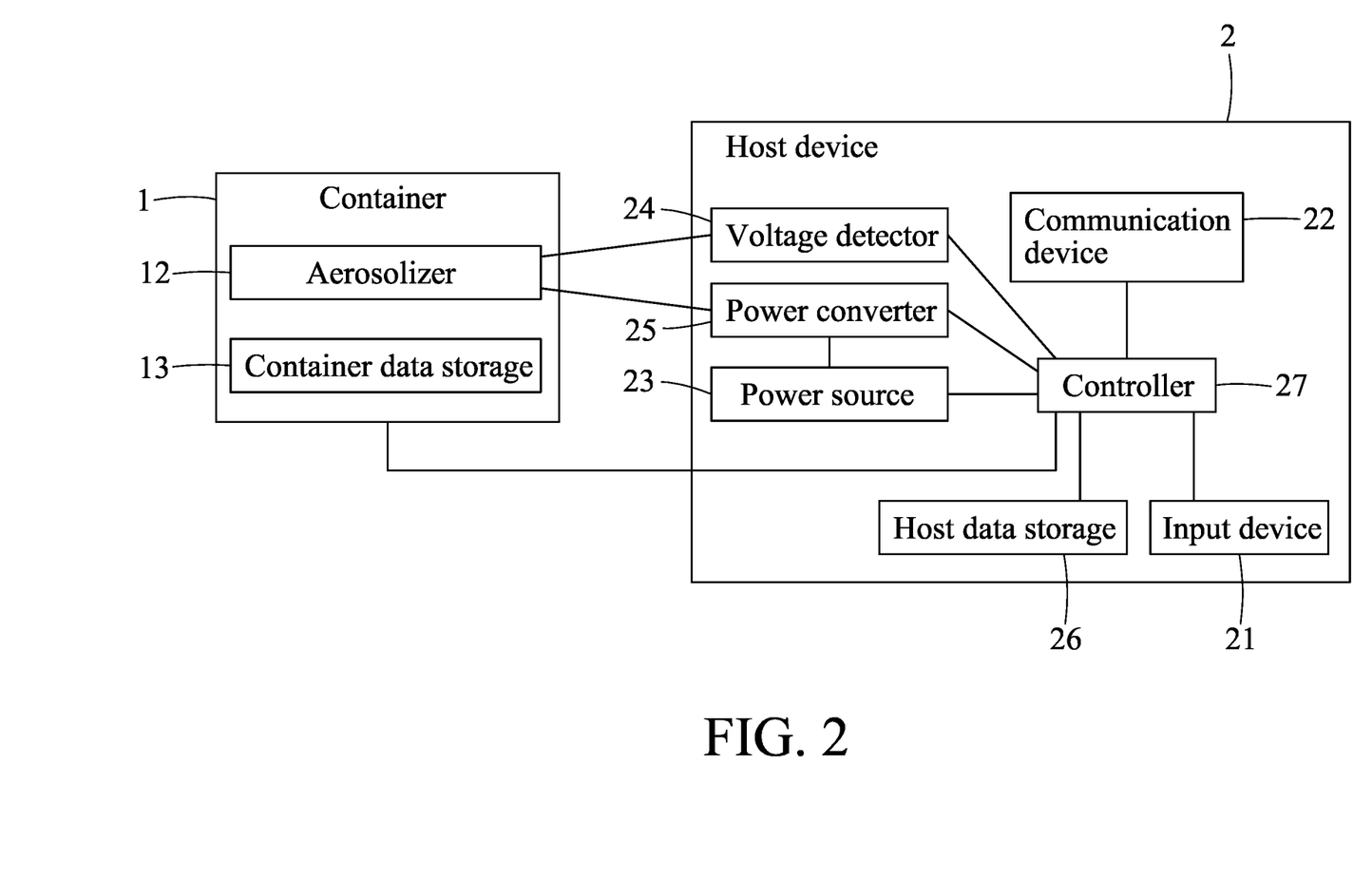
FIG. 2 is a block diagram illustrating the embodiment of the nebulizer according to the disclosure.

Referring to FIGS. 1 and 2, an embodiment of a nebulizer capable of calibrating spraying speed is illustrated. The nebulizer includes a container 1 and a host device 2 separably coupled to the container 1.

The container 1 includes a containing body 11 that is configured to accommodate liquid, an aerosolizer 12 that is disposed on the containing body 11, and a container data storage 13 that is disposed on the containing body 11.

The aerosolizer 12 is configured to aerosolize the liquid accommodated in the containing body 11 by vibration to result in aerosolized liquid, and to eject the aerosolized liquid. In this embodiment, the aerosolizer 12 is implemented to be a vibrator including a nozzle plate (not shown) and a piezoelectric plate (not shown), but is not limited thereto.

The container data storage 13 is configured to store a standard resonant-frequency value which corresponds to a standard spraying speed of the aerosolizer 12, and an expected feedback-voltage value which is related to the standard resonant-frequency value. In the following descriptions, the spraying speed is defined as an amount of the aerosolized liquid being ejected per unit of time. In this embodiment, the container data storage 13 is implemented by flash memory, a hard disk drive (HDD) or a solid state disk (SSD), an electrically-erasable programmable read-only memory (EEPROM) or any other non-volatile memory devices, but implementation of the container data storage 13 is not limited to the disclosure herein and may vary in other embodiments.

The host device 2 includes an input device 21 that is configured to be operated by a user for generating an input signal, a communication device 22 that is configured to be connected to and to receive signals from an external device, a power source 23 that is configured to supply electric power to the container 1, a voltage detector 24 that is electrically connected to the aerosolizer 12, a power converter 25 that is electrically connected to the power source 23 and the aerosolizer 12, a host data storage 26, and a controller 27 that is electrically connected to the aerosolizer 12, the container data storage 13, the input device 21, the communication device 22, the power source 23, the voltage detector 24, the power converter 25 and the host data storage 26.

In this embodiment, the input device 21 is implemented by a physical button set (a set of one or more physical buttons) or a touchscreen, but implementation of the input device 21 is not limited to the disclosure herein and may vary in other embodiments.

In this embodiment, the communication device 22 is implemented to be a network interface controller or a wireless transceiver that supports wired/wireless communication standards, but implementation of the communication device 22 is not limited to the disclosure herein and may vary in other embodiments.

In this embodiment, the power source 23 is implemented to be a battery or a power supply, but implementation of the power source 23 is not limited to the disclosure herein and may vary in other embodiments.

The voltage detector 24 is configured to continuously detect a feedback voltage coming from the aerosolizer 12 when the aerosolizer 12 is in operation to eject the aerosolized liquid, and generate a detected feedback-voltage value which indicates a current measurement result of the feedback voltage. In this embodiment, the voltage detector 24 detects a voltage across a resistor of the aerosolizer 12, and is implemented to include an analog-to-digital converter (ADC), a voltage meter or any circuit configurable/programmable in a software manner and/or hardware manner to implement functionalities described in relation to the voltage detector 24 in this disclosure. The expected feedback-voltage value is a value of the feedback voltage that is expected to be detected when a standardized aerosolizer, which has passed quality control (QC) testing before leaving the factory, is powered according to the standard resonant-frequency value by the power converter 25.

The power converter 25 is configured to convert the electric power supplied by the power source 23 by changing at least one of voltage or frequency of the electric power (i.e., the voltage and/or the frequency of the electric power), and to provide the electric power thus converted to the aerosolizer 12. In this embodiment, the power converter 25 is implemented to be a transformer or a second-order RLC circuit for voltage boosting, but implementation of the power converter 25 is not limited to the disclosure herein and may vary in other embodiments.

The host data storage 26 is configured to store a plurality of voltage-adjusting values which respectively correspond to a plurality of expected spraying speeds of the aerosolizer 12. Similar to the container data storage 13, the host data storage 26 may be implemented by flash memory, an HDD, an SSD, an EEPROM or any other non-volatile memory devices, but implementation of the host data storage 26 is not limited to the disclosure herein and may vary in other embodiments.

In this embodiment, the controller 27 may be implemented by a central processing unit (CPU), a microprocessor, a micro control unit (MCU), or any circuit configurable/programmable in a software manner and/or hardware manner to implement functionalities of the controller 27 disclosed herein.

In response to receipt of the input signal that requests operation of the aerosolizer 12 at the standard spraying speed (i.e., that requests the aerosolizer 12 to spray the aerosolized liquid at the standard spraying speed), the controller 27 is configured to read the standard resonant-frequency value stored in the container data storage 13, to make a parameter value of a conversion parameter equal the standard resonant-frequency value, to transmit the parameter value to the power converter 25, and to control the power source 23 to supply electric power. Then, the power converter 25 is configured to convert the electric power supplied by the power source 23 into converted electric power based on the parameter value, and to provide the converted electric power to the aerosolizer 12 so as to enable the aerosolizer 12 to vibrate based on the converted electric power. Further, the controller 27 is configured to, based on the continuously-generated detected feedback-voltage value from the voltage detector 24 and the expected feedback-voltage value stored in the container data storage 13, repeatedly control the power source 23 to adjust the voltage of the electric power supplied thereby (e.g., by a predetermined amount, such as by 0.1 volts for each adjustment) until it is determined that the detected feedback-voltage value matches the expected feedback-voltage value.

Specifically speaking, during adjustment of the voltage of the electric power, the controller 27 is configured to determine whether a difference between the detected feedback-voltage value and the expected feedback-voltage value (hereinafter also referred to as "voltage difference" for short) is smaller than a first threshold. The controller 27 is configured to determine that the detected feedback-voltage value matches the expected feedback-voltage value when it is determined that the voltage difference is smaller than the first threshold. If it is determined that the voltage difference is not smaller than the first threshold, the controller 27 keeps adjusting the voltage of the electric power supplied by the power source 23 for reducing the voltage difference.

However, when the controller 27 determines that it is unfeasible to reduce the voltage difference to be smaller than the first threshold by simply adjusting the voltage of the electric power supplied by the power source 23 (i.e., the mere act of adjusting the voltage of the electric power supplied by the power source 23 cannot cause the difference between the detected feedback-voltage value and the expected feedback-voltage value to fall below the first threshold), the controller 27 is configured to determine whether the voltage difference is smaller than a second threshold. It should be noted that the second threshold is greater than the first threshold. In one embodiment, an absolute value of the voltage difference is first calculated before comparison with the first threshold and/or the second threshold.

It is worth to note that there are two approaches to determining whether it is unfeasible to reduce the voltage difference to be smaller than the first threshold by adjusting the voltage of the electric power supplied by the power source 23.

In one approach, the controller 27 is configured to count a number of times the controller 27 has controlled the power source 23 to adjust the voltage of the electric power supplied thereby when it is determined that the voltage difference is not smaller than the first threshold, and to determine, based on the number of times thus counted, whether it is unfeasible to reduce the voltage difference to be smaller than the first threshold by adjusting the voltage of the electric power supplied by the power source 23. In this approach, when the number of times thus counted is greater than a predetermined integer (e.g., 10), the controller 27 determines that it is unfeasible to reduce the voltage difference to be smaller than the first threshold by adjusting the voltage of the electric power supplied by the power source 23.

In another approach, the controller 27 is configured to start a timer when it is determined for the first time that the voltage difference is not smaller than the first threshold, and to determine, based on elapsed time measured by the timer, whether it is unfeasible to reduce the voltage difference to be smaller than the first threshold by adjusting the voltage of the electric power supplied by the power source 23. The timer stops when it is determined that the voltage difference is smaller than the first threshold. In this embodiment, when the elapsed time thus measured is longer than a predetermined time duration (e.g., 10 minutes), the controller 27 determines that it is unfeasible to reduce the voltage difference to be smaller than the first threshold by adjusting the voltage of the electric power supplied by the power source 23.

After determining that reducing the voltage difference to be smaller than the first threshold by simply adjusting the voltage of the electric power supplied by the power source 23 is not feasible, when it is determined that the voltage difference is not smaller than the second threshold, the controller 27 is configured to repeatedly control the power source 23 to adjust the voltage of the electric power supplied thereby until it is determined that the voltage difference is smaller than the second threshold. After it has been determined that the voltage difference is smaller than the second threshold, the controller 27 is configured to update the parameter value of the conversion parameter based on the parameter value previously transmitted to the power converter 25, and to transmit the updated parameter value to the power converter 25 so as to enable the power converter 25 to convert the electric power supplied by the power source 23 into the converted electric power based on the updated parameter value for provision of the converted electric power to the aerosolizer 12. Subsequently, the controller 27 is configured to repeatedly update and transmit the parameter value of the conversion parameter to the power converter 25 for tuning the converted electric power provided to the aerosolizer 12 until it is determined that the voltage difference is smaller than the first threshold.

It is worth to note that correspondence relationships between the parameter values of the conversion parameter and voltages of the converted electric power may be determined in advance based on laboratory experiments, and may be recorded in a pre-established look-up table or a database. In this way, the power converter 25 is configured to convert the electric power supplied by the power source 23 into the converted electric power by means of referencing the pre-established look-up table or exploiting the database.

In some cases, the nebulizer may be adjusted to spray the aerosolized liquid at a target spraying speed which is one of the expected spraying speeds. In response to receipt of another input signal that requests operation of the aerosolizer 12 at the target spraying speed, the controller 27 is configured to obtain a target voltage value based on the detected feedback-voltage value and one of the voltage-adjusting values that corresponds to the target spraying speed, where the target voltage value indicates a difference between the detected feedback-voltage value and said one of the voltage-adjusting values that corresponds to the target spraying speed, and the difference needs to be offset to allow the nebulizer to spray the aerosolized liquid at the target spraying speed. Then, the controller 27 is configured to control the power source 23 to supply the electric power based on the target voltage value so that the aerosolizer 12 sprays the aerosolized liquid at the target spraying speed.

Figure 3:
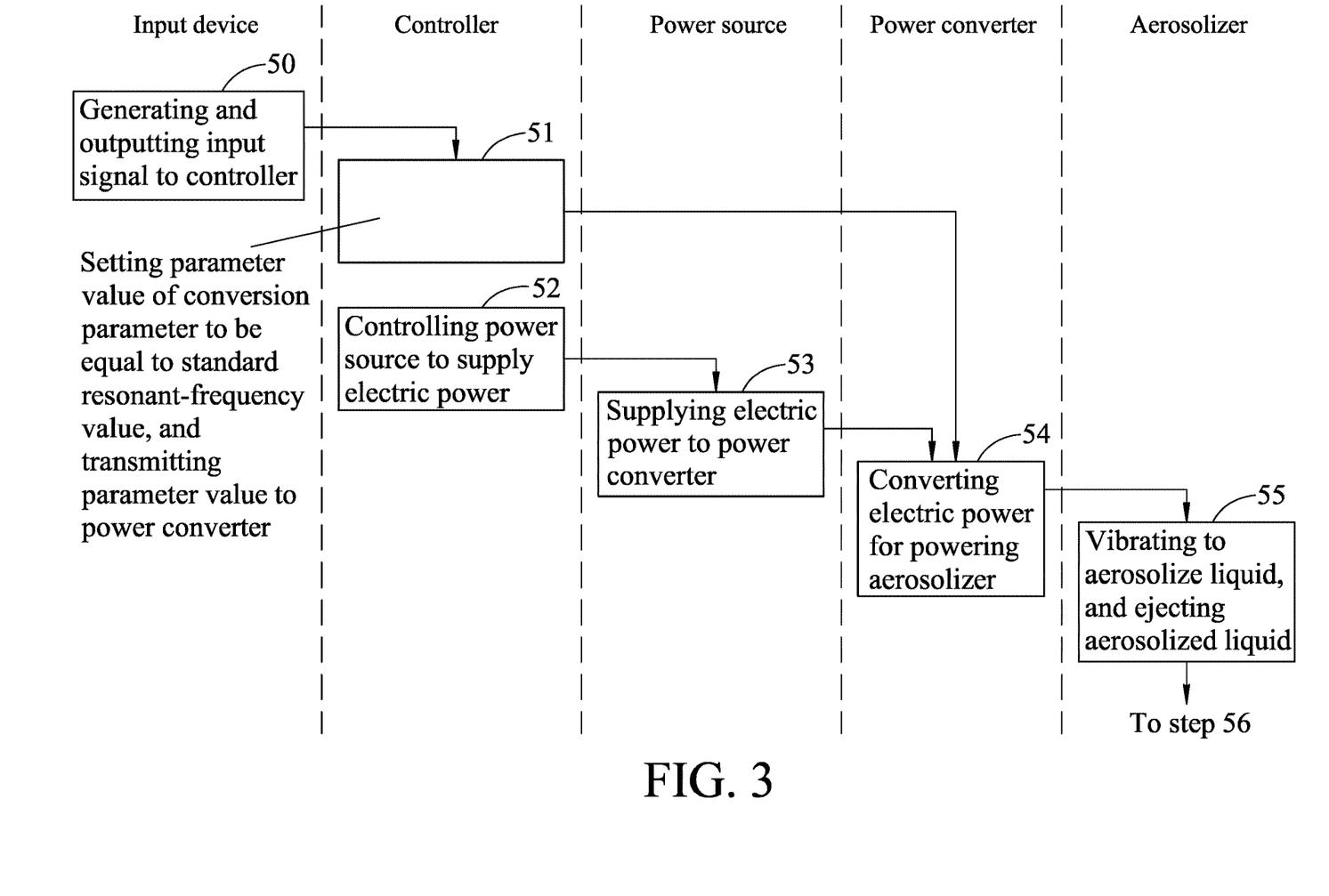
FIGS. 3 to 5 cooperatively constitute a flow chart for illustrating an embodiment of a calibration procedure of a method for calibrating spraying speed of the nebulizer according to the disclosure.
Figure 4:
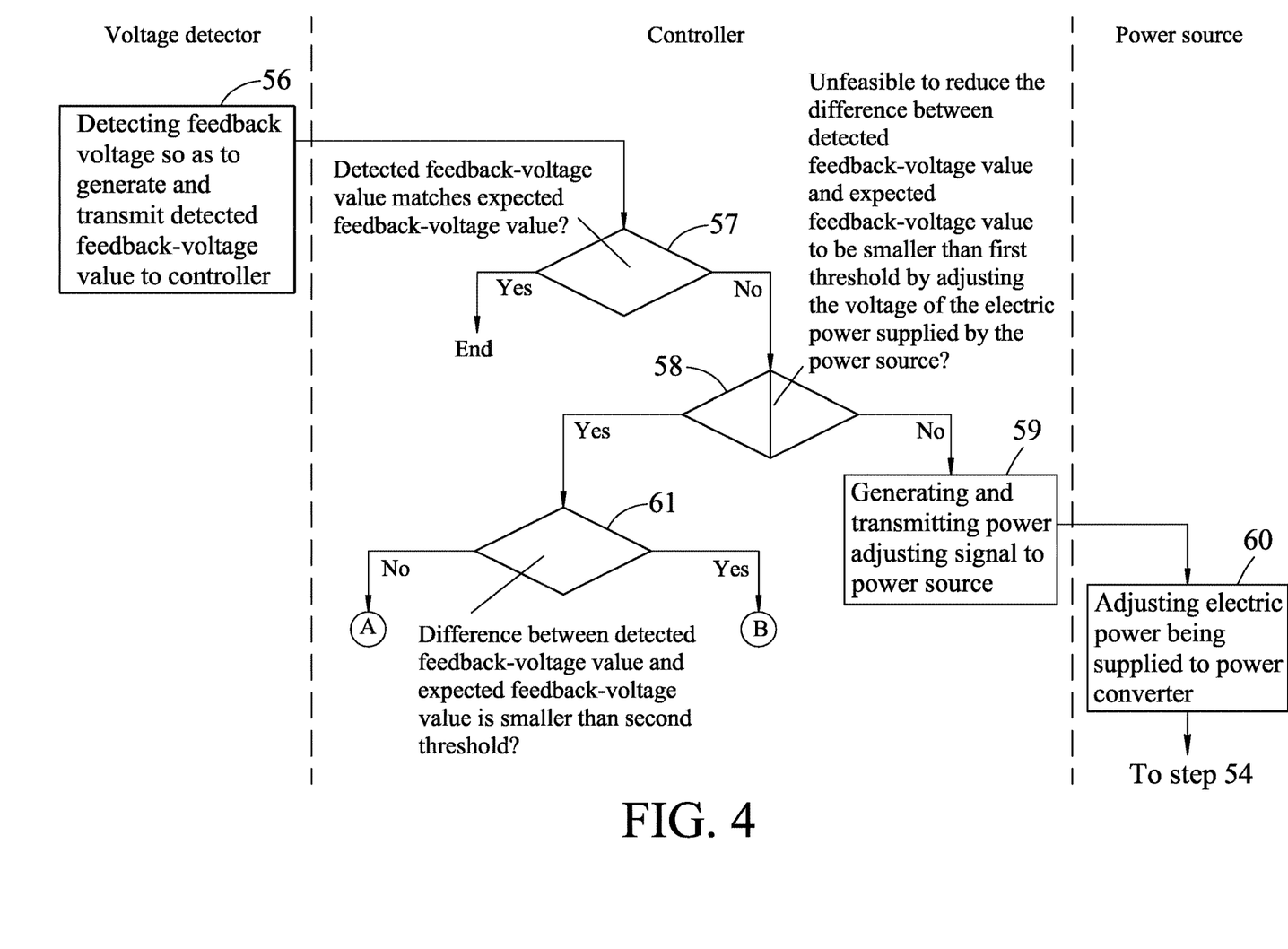
Figure 5:
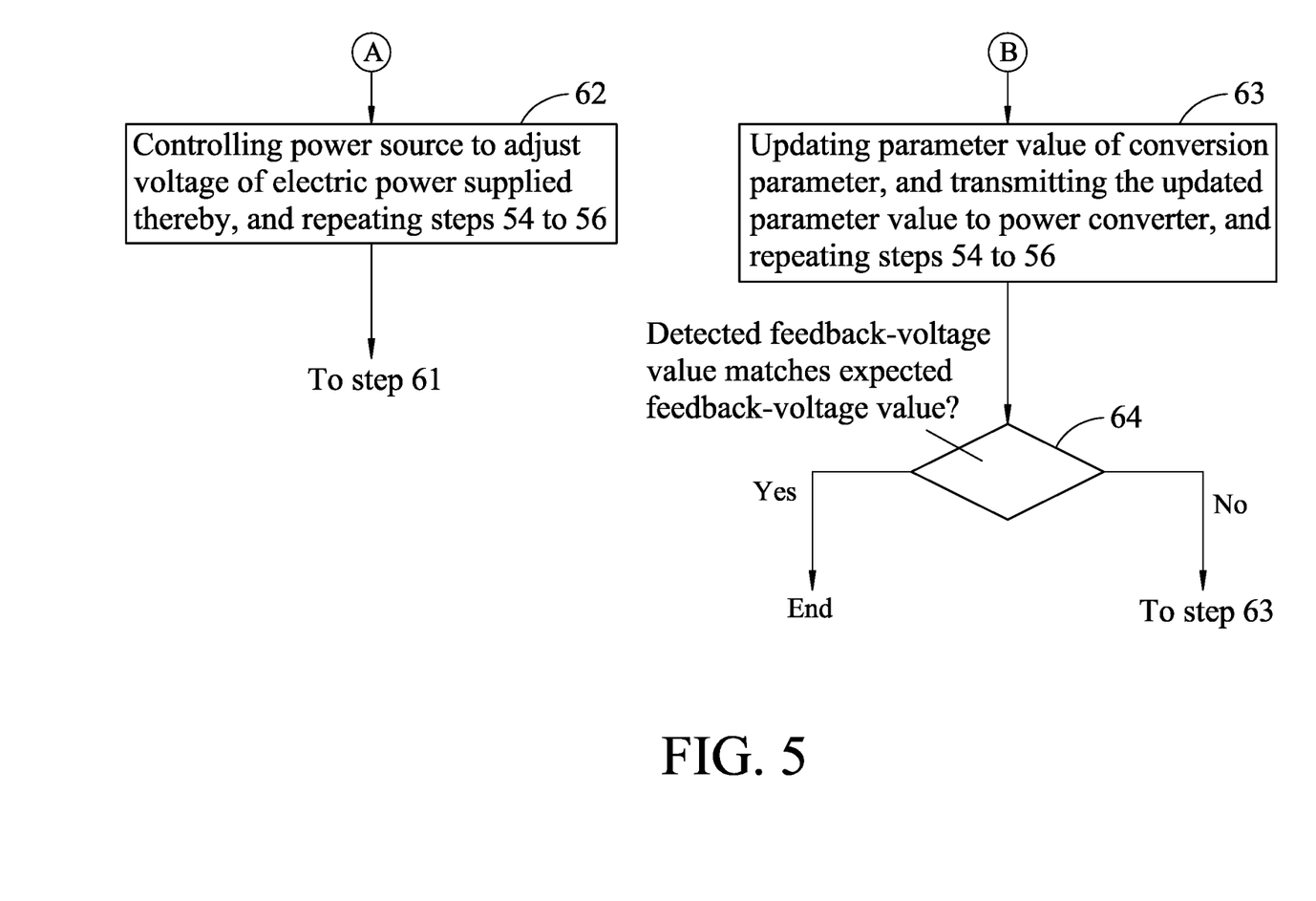

Referring to FIGS. 3 to 6, an embodiment of a method for calibrating spraying speed of the nebulizer is illustrated. The method includes a calibration procedure and an adjustment procedure. Referring to FIGS. 3 to 5, the calibration procedure includes steps 50 to 64 that are outlined below.

In step 50, the input device 21 is operated by the user to generate an input signal that requests operation of the aerosolizer 12 at the standard spraying speed, and outputs the input signal to the controller 27 via a wired electrical connection. It is worth to note that in some embodiments, the input signal is wirelessly transmitted by an external device (e.g., a smartphone) to the controller 27 via the communication device 22.

In step 51, in response to receipt of the input signal, the controller 27 reads the standard resonant-frequency value stored in the container data storage 13, makes the parameter value of the conversion parameter equal the standard resonant-frequency value, and transmits the parameter value to the power converter 25. It should be noted that in some embodiments, the controller 27 is configured to read the standard resonant-frequency value stored in the container data storage 13 via physical wiring or through wireless communication such as near-field communication (NFC).

In step 52, the controller 27 generates and transmits a power provision signal to the power source 23 to control the power source 23 to supply electric power.

In step 53, in response to receipt of the power provision signal, the power source 23 supplies the electric power to the power converter 25.

In step 54, based on the parameter value, the power converter 25 converts (e.g., through voltage step-up operation and/or frequency conversion) the electric power supplied by the power source 23 into the converted electric power, and provides the converted electric power to the aerosolizer 12.

In step 55, based on the converted electric power, the aerosolizer 12 vibrates so as to aerosolize the liquid accommodated in the containing body 11, and then ejects the aerosolized liquid.

In step 56, the voltage detector 24 detects the feedback voltage from the aerosolizer 12, generates the detected feedback-voltage value, and transmits the detected feedback-voltage value to the controller 27.

In step 57, based on the detected feedback-voltage value generated by the voltage detector 24 and the expected feedback-voltage value stored in the container data storage 13, the controller 27 determines whether the detected feedback-voltage value matches the expected feedback-voltage value (i.e., whether the difference between the detected feedback-voltage value and the expected feedback-voltage value (namely the voltage difference) is smaller than the first threshold). When it is determined by the controller 27 that the detected feedback-voltage value matches the expected feedback-voltage value, a flow of the calibration procedure comes to an end. That is to say, calibration of the nebulizer is successfully completed so the aerosolizer 12 of the nebulizer is capable of spraying the aerosolized liquid at the standard spraying speed, as required by the input signal. Otherwise, when it is determined by the controller 27 that the detected feedback-voltage value does not match the expected feedback-voltage value, the flow proceeds to step 58.

In step 58, the controller 27 determines whether reducing the voltage difference to be smaller than the first threshold by adjusting the voltage of the electric power supplied by the power source 23 is unfeasible. When it is determined by the controller 27 that doing so is unfeasible, the flow of the calibration procedure proceeds to step 61. Otherwise, the flow proceeds to step 59.

In step 59, based on the detected feedback-voltage value and the expected feedback-voltage value, the controller 27 generates and transmits a power adjusting signal to the power source 23. In this embodiment, the power adjusting signal is a periodic signal with a specific duty cycle for controlling voltage output of the power source 23, wherein the specific duty cycle is determined based on the detected feedback-voltage value and the expected feedback-voltage value.

In step 60, in response to receipt of the power adjusting signal, the power source 23 adjusts, by voltage step-down operation or voltage step-up operation based on the power adjusting signal, the electric power that is being supplied to the power converter 25 by the predetermined amount (e.g., 0.1 volts). Thereafter, the flow returns to step 54.

In step 61, the controller 27 determines whether the voltage difference is smaller than the second threshold. When it is determined that the voltage difference is not smaller than the second threshold, the flow proceeds to step 62. Oppositely, when it is determined that the voltage difference is smaller than the second threshold, the flow proceeds to step 63.

In step 62, based on the detected feedback-voltage value and the expected feedback-voltage value, the controller 27 generates and transmits the power adjusting signal to the power source 23 so as to control the power source 23 to adjust, by voltage step-down operation or voltage step-up operation, the voltage of the electric power supplied by the power source 23. At this time, conversion by the power converter 25 of the electric power supplied by the power source 23 into the converted electric power is still performed based on the same parameter value. With the voltage having been adjusted and the operation of the power converter 25, the aerosolizer 12 and the voltage detector 24 carried out in the same manner as before, the detected feedback-voltage value transmitted to the controller 27 should be different from before. The flow returns to step 61 after step 62, allowing the controller 27 to determine whether a difference between the (new) detected feedback-voltage value and the expected feedback-voltage value is smaller than the second threshold.

In step 63, the controller 27 updates the parameter value of the conversion parameter based on the parameter value previously transmitted to the power converter 25, and transmits the updated parameter value to the power converter 25. The power converter 25 converts the electric power supplied by the power source 23 into the converted electric power based on the updated parameter value, and provides the converted electric power to the aerosolizer 12. With conversion of the electric power based on the updated parameter value, and operation of the aerosolizer 12 and the voltage detector 24 carried out in the same manner as before, the detected feedback-voltage value transmitted to the controller 27 should be different from before. Next, the flow proceeds to step 64.

In step 64, in response to receipt of the (new) detected feedback-voltage value, the controller 27 determines whether the (new) detected feedback-voltage value matches the expected feedback-voltage value (i.e., the difference between the (new) detected feedback-voltage value and the expected feedback-voltage value is smaller than the first threshold). When it is determined by the controller 27 that the (new) detected feedback-voltage value matches the expected feedback-voltage value, the flow terminates. In this way, the nebulizer is successfully calibrated and is capable of spraying the aerosolized liquid at the standard spraying speed. Otherwise, when it is determined by the controller 27 that the (new) detected feedback-voltage value does not match the expected feedback-voltage value, the flow returns to step 63 to perform further calibration.

It is worth to note that by the controller 27 which updates the parameter value of the conversion parameter each time before the parameter value is to be transmitted to the power converter 25, the power converter 25 is able to keep adjusting the converted electric power provided to the aerosolizer 12 until it is determined that the detected feedback-voltage value matches the expected feedback-voltage value. Vibration of the aerosolizer 12 varies in response to receipt of different converted electric power from the power converter 25, and the detected feedback-voltage value generated by the voltage detector 24 also varies accordingly.

Moreover, the converted electric power outputted by the power converter 25 is more sensitive to variation in the electric power outputted by the power source 23 than to variation in the parameter value of the conversion parameter received from the controller 27. Consequently, adjusting the electric power outputted by the power source 23 results in an effect of coarse adjustment of the detected feedback-voltage value which is performed at the initial stage of the calibration procedure, and adjusting the parameter value results in an effect of fine adjustment of the detected feedback-voltage value which is performed in a condition that the difference between the detected feedback-voltage value and the expected feedback-voltage value is not smaller than the first threshold but is smaller than the second threshold.

Figure 6:
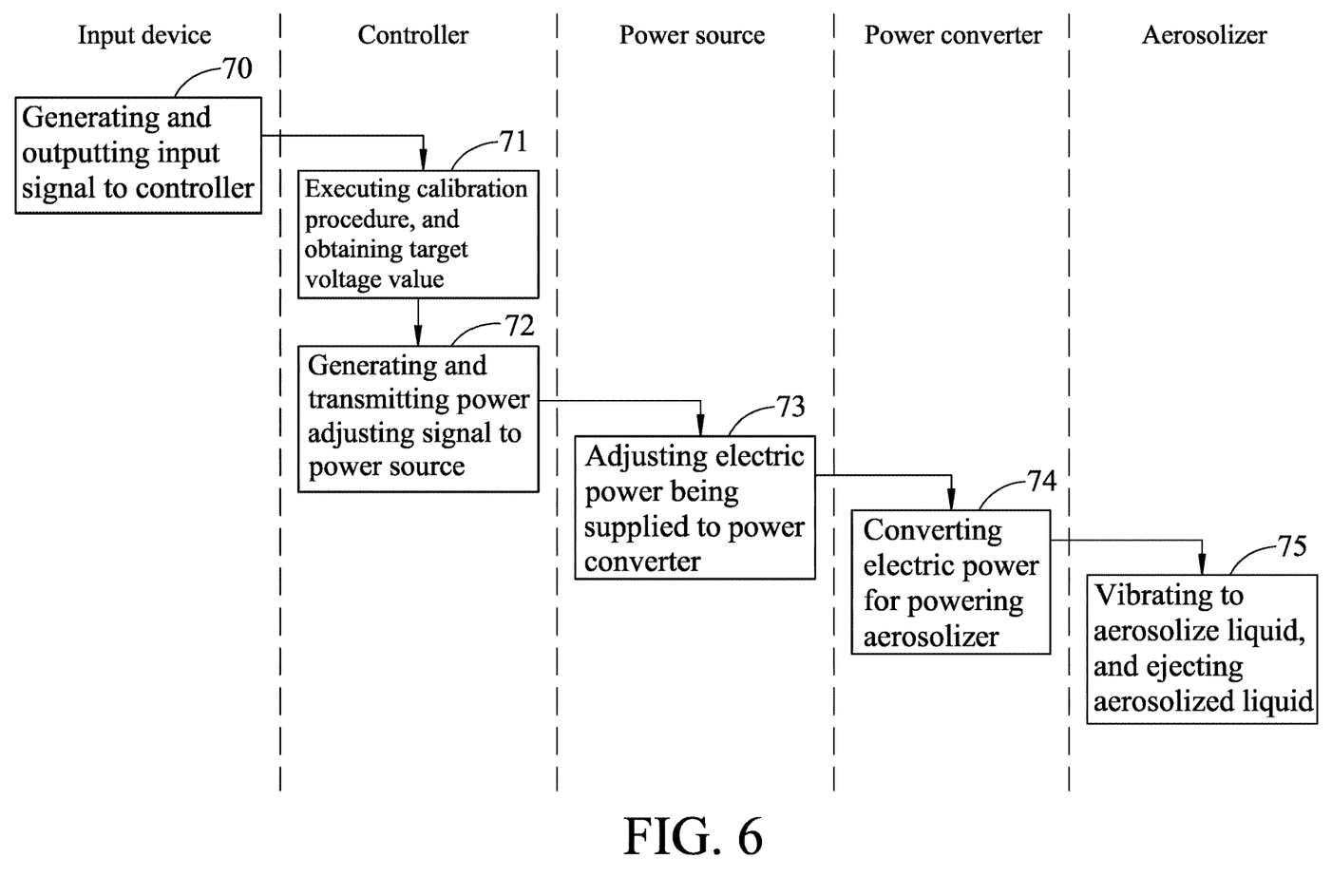
FIG. 6 is a flow chart illustrating an embodiment of an adjustment procedure of the method according to the disclosure.

Referring to FIG. 6, the adjustment procedure of the method includes steps 70 to 75 that are outlined below.

In step 70, the input device 21 is operated by the user to generate another input signal that requests operation of the aerosolizer 12 at a target spraying speed which is one of the expected spraying speeds, and outputs said another input signal to the controller 27.

In step 71, in response to receipt of said another input signal, the controller 27 performs the calibration procedure at first, and after the calibration procedure come to an end, obtains the target voltage value based on the most recent detected feedback-voltage value and one of the voltage-adjusting values corresponding to the target spraying speed.

In step 72, based on the target voltage value indicating the difference between the detected feedback-voltage value and said one of the voltage-adjusting values that corresponds to the target spraying speed, the controller 27 generates and transmits another power adjusting signal to the power source 23 for controlling voltage output of the power source 23 to offset the difference.

In step 73, in response to receipt of said another power adjusting signal, the power source 23 adjusts, by voltage step-down operation or voltage step-up operation based on said another power adjusting signal, the electric power that is being supplied to the power converter 25. It is noted that in step 73, the electric power is adjusted by the predetermined amount, e.g., +0.1 volts or −0.1 volts, and steps 71 to 73 may be performed repeatedly until the most recently detected feedback-voltage value matches said one of the voltage-adjusting values corresponding to the target spraying speed.

In step 74, the power converter 25 converts (e.g., through voltage step-up operation and/or frequency conversion) the electric power supplied by the power source 23 into the converted electric power based on the last parameter value obtained in the calibration procedure, and provides the converted electric power to the aerosolizer 12.

In step 75, the aerosolizer 12 vibrates based on the converted electric power so as to aerosolize the liquid accommodated in the containing body 11, and then ejects the aerosolized liquid at the target spraying speed.

In summary, the nebulizer according to the disclosure utilizes the voltage detector 24 to continuously obtain the detected feedback-voltage value. Moreover, the power source 23 is repeatedly controlled to adjust the voltage of the electric power supplied thereby, and/or the parameter value of the conversion parameter is repeatedly updated and outputted to the power converter 25 until it is determined by the controller 27 that the detected feedback-voltage value matches the expected feedback-voltage value. After the abovementioned adjustments/calibrations, the power source 23 and the power converter 25 can cooperate to provide the necessary converted electric power to drive the aerosolizer 12 to accurately eject the aerosolized liquid at the desired speed, be it one of the expected spraying speeds or the standard spraying speed.

In the description above, for the purposes of explanation, numerous specific details have been set forth in order to provide a thorough understanding of the embodiment. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. A nebulizer capable of calibrating spraying speed, comprising:
    a container including
        a containing body that is configured to accommodate liquid,
        an aerosolizer that is disposed on said containing body, and that is configured to aerosolize the liquid accommodated in said containing body by vibration to result in aerosolized liquid, and to eject the aerosolized liquid, and
        a container data storage that is disposed on said containing body, and that is configured to store a standard resonant-frequency value which corresponds to a standard spraying speed of said aerosolizer, and an expected feedback-voltage value which is related to the standard resonant-frequency value; and
    a host device separably coupled to said container, and including
        a power source that is configured to supply electric power,
        a power converter that is electrically connected to said power source and said aerosolizer,
        a voltage detector that is electrically connected to said aerosolizer, and that is configured to continuously detect a feedback voltage coming from said aerosolizer, and to generate a detected feedback-voltage value which indicates a current measurement result of the feedback voltage, and
        a controller that is electrically connected to said aerosolizer, said container data storage, said power source, said voltage detector and said power converter, and that is configured to, in response to receipt of an input signal that requests operation of said aerosolizer at the standard spraying speed, read the standard resonant-frequency value stored in said container data storage, make a parameter value of a conversion parameter equal the standard resonant-frequency value, transmit the parameter value to said power converter, and control said power source to supply electric power,
    wherein said power converter is further configured to, based on the conversion parameter, convert the electric power supplied by said power source into converted electric power by changing at least one of voltage or frequency of the electric power, and to provide the converted electric power to said aerosolizer so as to enable said aerosolizer to vibrate based on the converted electric power and to generate the feedback-voltage; and wherein said controller is further configured to, based on the detected feedback-voltage value generated by said voltage detector and the expected feedback-voltage value stored in said container data storage, repeatedly control said power source to adjust the voltage of the electric power supplied thereby until it is determined that the detected feedback-voltage value matches the expected feedback-voltage value.

2. The nebulizer as claimed in claim 1, wherein said controller is further configured to determine whether a difference between the detected feedback-voltage value and the expected feedback-voltage value is smaller than a first threshold, and to determine that the detected feedback-voltage value matches the expected feedback-voltage value when it is determined that the difference between the detected feedback-voltage value and the expected feedback-voltage value is smaller than the first threshold.

3. The nebulizer as claimed in claim 2, wherein said controller is further configured to:
when it is determined that it is unfeasible to reduce the difference between the detected feedback-voltage value and the expected feedback-voltage value to be smaller than the first threshold by adjusting the voltage of the electric power supplied by said power source, determine whether the difference between the detected feedback-voltage value and the expected feedback-voltage value is smaller than a second threshold;
when it is determined that the difference between the detected feedback-voltage value and the expected feedback-voltage value is not smaller than the second threshold, repeatedly control said power source to adjust the voltage of the electric power supplied thereby until it is determined that the difference between the detected feedback-voltage value and the expected feedback-voltage value is smaller than the second threshold; and
when it is determined that the difference between the detected feedback-voltage value and the expected feedback-voltage value is smaller than the second threshold, update the parameter value of the conversion parameter based on the parameter value previously transmitted to said power converter, transmit the parameter value thus updated to said power converter so as to enable said power converter to convert, based on the parameter value thus updated, the electric power supplied by said power source into the converted electric power for provision to said aerosolizer, and repeatedly update and transmit the parameter value to said power converter for tuning the converted electric power provided to said aerosolizer until it is determined that the difference between the detected feedback-voltage value and the expected feedback-voltage value is smaller than the first threshold.

4. The nebulizer as claimed in claim 3, wherein said controller is further configured to count the number of times said controller has controlled said power source to adjust the voltage of the electric power supplied thereby when it is determined that the difference between the detected feedback-voltage value and the expected feedback-voltage value is not smaller than the first threshold, and to determine, based on the number of times thus counted, whether it is unfeasible to reduce the difference between the detected feedback-voltage value and the expected feedback-voltage value to be smaller than the first threshold by adjusting the voltage of the electric power supplied by said power source.

5. The nebulizer as claimed in claim 3, wherein said controller is further configured to start a timer when it is determined for the first time that the difference between the detected feedback-voltage value and the expected feedback-voltage value is not smaller than the first threshold, and to determine, based on elapsed time measured by the timer, whether it is unfeasible to reduce the difference between the detected feedback-voltage value and the expected feedback-voltage value to be smaller than the first threshold by adjusting the voltage of the electric power supplied by said power source.

6. The nebulizer as claimed in claim 1, wherein:
said host device further includes a host data storage that is configured to store a plurality of voltage-adjusting values which respectively correspond to a plurality of expected spraying speeds of said aerosolizer; and
said controller is further configured to, in response to receipt of another input signal that requests operation of said aerosolizer at a target spraying speed which is one of the expected spraying speeds, obtain a target voltage value based on the detected feedback-voltage value and one of the voltage-adjusting values that corresponds to the target spraying speed, and to control said power source to supply the electric power based on the target voltage value so that said aerosolizer sprays the aerosolized liquid at the target spraying speed.

7. A method for calibrating spraying speed of a nebulizer, the nebulizer including a container and a host device, the container including a containing body that accommodates liquid, an aerosolizer that aerosolizes the liquid accommodated in the containing body by vibration to result in aerosolized liquid and ejects the aerosolized liquid, and a container data storage that stores a standard resonant-frequency value which corresponds to a standard spraying speed of the aerosolizer, and an expected feedback-voltage value which is related to the standard resonant-frequency value, the host device including a controller, a power source that supplies electric power, a power converter that converts the electric power supplied by the power source by changing at least one of voltage or frequency, and provides the electric power thus converted to the aerosolizer, and a voltage detector that continuously detects a feedback voltage coming from the aerosolizer, and generates a detected feedback-voltage value which indicates a current measurement result of the feedback voltage, the method comprising steps of:
a) by the controller in response to receipt of an input signal that requests operation of the aerosolizer at the standard spraying speed, reading the standard resonant-frequency value stored in the container data storage, making a parameter value of a conversion parameter equal the standard resonant-frequency value, transmitting the parameter value to the power converter, and controlling the power source to supply electric power;
b) by the power converter, converting the electric power supplied by the power source into converted electric power based on the parameter value, and providing the converted electric power to the aerosolizer so as to enable the aerosolizer to vibrate based on the converted electric power; and
c) by the controller based on the detected feedback-voltage value generated by the voltage detector and the expected feedback-voltage value stored in the container data storage, repeatedly controlling the power source to adjust the voltage of the electric power supplied thereby until it is determined that the detected feedback-voltage value matches the expected feedback-voltage value.

8. The method as claimed in claim 7, further comprising:
d) determining, by the controller, whether a difference between the detected feedback-voltage value and the expected feedback-voltage value is smaller than a first threshold; and
e) determining, by the controller, that the detected feedback-voltage value matches the expected feedback-voltage value when it is determined that the difference between the detected feedback-voltage value and the expected feedback-voltage value is smaller than the first threshold.

9. The method as claimed in claim 8, further comprising:
f) by the controller when it is determined that it is unfeasible to reduce the difference between the detected feedback-voltage value and the expected feedback-voltage value to be smaller than the first threshold by adjusting the voltage of the electric power supplied by the power source, determining whether the difference between the detected feedback-voltage value and the expected feedback-voltage value is smaller than a second threshold;
g) by the controller when it is determined that the difference between the detected feedback-voltage value and the expected feedback-voltage value is not smaller than the second threshold, repeatedly controlling the power source to adjust the voltage of the electric power supplied thereby until it is determined that the difference between the detected feedback-voltage value and the expected feedback-voltage value is smaller than the second threshold; and
h) by the controller when it is determined that the difference between the detected feedback-voltage value and the expected feedback-voltage value is smaller than the second threshold, updating the parameter value of the conversion parameter based on the parameter value previously transmitted to the power converter, transmitting the parameter value thus updated to the power converter so as to enable the power converter to convert, based on the conversion parameter thus updated, the electric power supplied by the power source into the converted electric power for provision to the aerosolizer, and repeatedly updating and transmitting the parameter value to the power converter for tuning the converted electric power provided to the aerosolizer until it is determined that the difference between the detected feedback-voltage value and the expected feedback-voltage value is smaller than the first threshold.

10. The method as claimed in claim 9, further comprising:
i) by the controller when it is determined that the difference between the detected feedback-voltage value and the expected feedback-voltage value is not smaller than the first threshold, counting the number of times the controller has controlled the power source to adjust the voltage of the electric power supplied thereby; and
j) determining, by the controller based on the number of times thus counted, whether it is unfeasible to reduce the difference between the detected feedback-voltage value and the expected feedback-voltage value to be smaller than the first threshold by adjusting the voltage of the electric power supplied by the power source.

11. The method as claimed in claim 9, further comprising:
k) by the controller when it is determined for the first time that the difference between the detected feedback-voltage value and the expected feedback-voltage value is not smaller than the first threshold, starting a timer; and
l) determining, by the controller based on elapsed time measured by the timer, whether it is unfeasible to reduce the difference between the detected feedback-voltage value and the expected feedback-voltage value to be smaller than the first threshold by adjusting the voltage of the electric power supplied by the power source.

12. The method as claimed in claim 7, the host device further including a host data storage that stores a plurality of voltage-adjusting values which respectively correspond to a plurality of expected spraying speeds of the aerosolizer, subsequent to step c), the method further comprising:
m) by the controller in response to receipt of another input signal that requests operation of the aerosolizer at a target spraying speed which is one of the expected spraying speeds, obtaining a target voltage value based on the detected feedback-voltage value and one of the voltage-adjusting values corresponding to the target spraying speed, and controlling the power source to supply the electric power based on the target voltage value so that the aerosolizer sprays the aerosolized liquid at the target spraying speed.

* * * * *